US009549736B2

(12) United States Patent
Barcroft et al.

(10) Patent No.: US 9,549,736 B2
(45) Date of Patent: Jan. 24, 2017

(54) SUTURELESS WOUND CLOSURE

(71) Applicant: Deva Medical Ventures Limited, Chester (GB)

(72) Inventors: Anthony Barcroft, Chester (GB); Peter Brownson, Chester (GB)

(73) Assignee: Deva Medical Ventures Limited, Chester (GB)

( * ) Notice: Subject to any disclaimer, the term of this patent is extended or adjusted under 35 U.S.C. 154(b) by 0 days.

(21) Appl. No.: 14/401,912

(22) PCT Filed: Jun. 5, 2014

(86) PCT No.: PCT/GB2014/051735
§ 371 (c)(1),
(2) Date: Nov. 18, 2014

(87) PCT Pub. No.: WO2014/195710
PCT Pub. Date: Dec. 11, 2014

(65) Prior Publication Data
US 2015/0173758 A1 Jun. 25, 2015

(30) Foreign Application Priority Data
Jun. 7, 2013 (GB) .................................. 1310190.2

(51) Int. Cl.
*A61B 17/08* (2006.01)
*A61F 13/02* (2006.01)
*A61F 13/00* (2006.01)

(52) U.S. Cl.
CPC ............. *A61B 17/08* (2013.01); *A61B 17/085* (2013.01); *A61F 13/0223* (2013.01); *A61F 13/0226* (2013.01); *A61F 13/0246* (2013.01); *A61B 2017/081* (2013.01); *A61B 2017/086* (2013.01); *A61F 2013/0057* (2013.01);
(Continued)

(58) Field of Classification Search
CPC . A61B 17/08; A61B 17/085; A61B 2017/081; A61B 2017/86; A61F 13/02; A61F 2013/00553; A61F 2013/00455; A61F 2013/0057; A61F 2013/00468
See application file for complete search history.

(56) References Cited

U.S. PATENT DOCUMENTS 2,722,220 A * 11/1955 Mestrand ............ A61B 17/085
606/215
4,423,731 A 1/1984 Roomi
(Continued)

FOREIGN PATENT DOCUMENTS

DE          4400713 A1   7/1995
WO   WO 2012/092121 A1   7/2012

OTHER PUBLICATIONS

International Search Report for PCT/GB2014/051735, dated Aug. 25, 2014 (4 pages).

*Primary Examiner* — Ashley Fishback
(74) *Attorney, Agent, or Firm* — Bookoff McAndrews, PLLC

(57) ABSTRACT

The present invention resides in a sutureless wound closure device for external use. The device comprises a base layer for fixing the device to skin and an upper layer. The base layer includes an aperture therein. The upper layer has a first end anchored to the base layer and a second, opposite end that includes fixing means to attach the end to the base layer and close the aperture in the base layer.

18 Claims, 5 Drawing Sheets

(52) U.S. Cl.
CPC ........... *A61F 2013/00455* (2013.01); *A61F 2013/00468* (2013.01); *A61F 2013/00553* (2013.01)

(56) References Cited

U.S. PATENT DOCUMENTS

| | | | |
|---|---|---|---|
| 5,176,703 A | 1/1993 | Peterson | |
| 2002/0015726 A1* | 2/2002 | Scamilla Aledo | A61F 13/0203 |
| | | | 424/446 |
| 2003/0032910 A1 | 2/2003 | Oyaski | |
| 2005/0284801 A1 | 12/2005 | Tacklind | |
| 2012/0016410 A1* | 1/2012 | Belson | A61B 17/085 |
| | | | 606/213 |

* cited by examiner

SUTURELESS WOUND CLOSURE

This application is a national stage filing under 35 U.S.C. §371 of International Application No. PCT/GB2014/051735, filed on Jun. 5, 2014, incorporated by reference herein in its entirety, which published in the English language and claims the benefit of priority to United Kingdom Patent Application No. 1310190.2, filed on Jun. 7, 2013.

The present invention relates to a device and technique to close wounds without the use of sutures.

Surgery requires cutting of the skin to reveal underlying tissues on which medical intervention is required. An increasingly popular alternative to open surgery is keyhole surgery, in which a number of small incisions or punctures of typically 5 to 10 mm in length are made to allow access to the underlying tissues and body structures. Surgery is then carried out using hand-held or robotically controlled telescopes and micro-instruments. There are a number of advantages for a patient with keyhole surgery versus an open procedure. These include reduced pain due to smaller incisions, reduced tissue damage and shorter recovery time.

Keyhole surgery usually results in multiple small incisions. Surgeons have a number of options in terms of wound closure once surgery is completed. The most time efficient method for the surgeon is to leave the wounds to heal on their own, particularly smaller wounds. However, the wounds usually weep and typically require redressing. The wound may also not repair cleanly, leaving visible scarring.

While a simple dressing may be applied to the wound to soak up any seepage, such a dressing will not close the wound, which is particularly important because, whilst the incision will be made in a straight line, the aperture will have become elliptical during surgery and so needs to be returned to a straight line to reduce wound seepage and limit scarring.

Some surgeons prefer suturing of the wounds, particularly the larger wounds (10-15 mm). Suturing is technically difficult especially in the smaller wounds and is therefore time consuming. Sutures themselves have a financial cost and leave a foreign material within the wound which is a nidus for infection. If non absorbable sutures are used, the suture needs to be removed at some stage following the surgery (typically 5-10 days) and the sutures themselves may produce scarring compromising the cosmetic result. Absorbable sutures although not requiring removal, may produce an inflammatory reaction in some patients.

An alternative technique of wound closure is the use of so called "butterfly stitches". Typical commercially available products are Steri-Strips™ or Micropore™ Surgical Tape. Steri-Strips are thin adhesive strips reinforced with polyester filaments that are applied across a laceration. The primary purpose of applying a Steri-Strip type product across a wound opening is to close the wound and prevent the wound from opening further. The way in which this is done typically involves placing the adhesive Steri-Strip onto either side of the wound in a manner that pulls the skin on either side of the wound together. Steri-Strips lessen scarring, reduce the chance of infection compared to sutures or staples, provide wound support and are easier to care for.

However, there are two big drawbacks of using Steristrips to close small wounds, particularly those resulting from keyhole surgery. Firstly, wounds from keyhole surgery notoriously weep fluids (blood and other fluids like saline, used to irrigate during surgery). When a Steri-strip is used, fluid exudes from the wound as it is squeezed shut. As the Steri-Strip is placed across the wound, this fluid wicks along both axes of the Steri-Strip, dramatically reducing adhesive properties of the Steri-Strip and preventing adequate skin adhesion to maintain wound closure.

Secondly, whilst a Steri-Strip, correctly applied across a wound, can prevent a wound from opening further, they do not provide an easy and reproducible method of closing the wound edges to encourage scar free healing and reduced risk of infection.

U.S. Pat. No. 7,927,347 describes an array of existing sutureless devices, as well as the device claimed therein. For example, U.S. Pat. No. 3,971,384 describes a surgical closure device having two pieces of surgical tape that are secured on each side of a wound. One piece of tape has an anchor for a tie strip secured to it while the other piece of tape has a slide secured to it. The tie strip has ratchet teeth on its dorsal surface so that the strip is inserted through the anchor end, across the wound and into the ratchet. The tape is then tightened and locked with the ratchet bringing the two sides of the wound together. This a cumbersome and complicated piece of equipment more suited to lengthy wounds and as such is deemed as unsuitable for small puncture wounds as found in keyhole surgery.

U.S. Pat. No. 4,924,866 describes a wound closure device comprising two arms connected by a hinged joint. The arms each have a single pair of "skin engaging members" on the ventral surface so that, when the device is placed over a wound, the skin engaging members enter the skin, pulling the wound together underneath the joint. Not only is this device limited in its pliability because of the structure of the arms, but the use of barbs in close proximity to the wound brings its wound closure ability into question. The lack of a ratchet mechanism also means that the edges of the wound must be juxtaposed before the device is applied. Last but not least, such a device is rather bulky and clunky for a small wound closure.

U.S. Pat. No. 7,927,347 itself describes a surgical fastener which is adhered to the skin by barbs and closes the two sides of a wound by way of male and female interconnecting straps that are tensioned using a ratchet mechanism. Again, the device itself is bulky and over complicated for the task in hand.

Thus, there is a need for sutureless wound closures that are effective when used in a damp or moist environment and employ a swift and durable application technique.

Accordingly, the present invention resides in a simple wound closure device that is quick to apply, simple, quick and effective to operate and cheap to manufacture.

In particular, the present invention resides in a sutureless wound closure device comprising: a) a base layer for attaching the device to skin; and b) an upper tensioning layer having a first end anchored to the base layer and a second, opposite end including fixing means to attach the end to the base layer, wherein the base layer includes an aperture that, in use, is covered by the upper tensioning layer.

The base layer provides a firm attachment for the device on the skin and the aperture allows any exudate or fluid to escape from the wound without being wicked along the base layer and causing the base layer to be released from the skin. The upper layer covers the aperture and allows the sides of the wound or incision to be juxtaposed and substantially closed through tension of the upper layer on the base layer. The aperture also acts to support the wound or incision while it heals, and substantially prevents bunching of redundant dressing when tension is applied to the upper tensioning layer.

The device is for external use to close a wound or incision in the skin.

The base layer may be any suitable shape but is preferably substantially rectangular in shape having a length greater than its width.

It will be appreciated that the base layer needs to be attachable to the skin in a non-permanent fashion. However, the bond between the skin and base layer should be strong enough to allow the device to remain in position for a suitable number of days or weeks, without moving or becoming dislodged by clothing or washing, to allow the wound to close and heal sufficiently. Thus, ideally, the base layer includes a (hypoallergenic) self-adhesive layer but may equally well include adhesive, barbs or microneedles on its skin-facing surface to attach the device to the skin.

The base layer may be made from any suitable material, such as a non-woven, paper-based material such as that used for surgical tape or Micropore™. If such a material is used, then it may be necessary to reinforce the material, for example by using polyester filaments running the length of the base layer, as used in Steri-strips. Alternatively, the base layer may be made from a plasticised material or a polymer that has suitable strength and durability for the intended use. In essence, because the base layer includes an aperture, it should be constructed from a material that has sufficient integral strength to withstand the inclusion of an aperture therein.

For ease of location of the device in use, the aperture is preferably located substantially centrally in the width and length of the base layer. However, it will be appreciated that the aperture may be located anywhere along the length and/or width of the device, provided that the base layer maintains sufficient integral strength; i.e. is not prone to tearing in use.

The aperture may be of any suitable shape and size. In use, the aperture is ideally sized substantially to surround an incision or wound in the skin. In particular, a substantially elliptical shape, orientated perpendicular to the length of the base layer, is believed to be the optimum shape. In this way, the user is able to view the wound or incision through the aperture to ensure that the wound is correctly positioned with respect to the aperture and supported by the base layer when applied to the skin. Also, since a straight incision will become elliptical during surgery, the base layer aperture will roughly mimic the shape of the wound and, as will be explained later, will enable an accurate juxtaposition of the two opposing sides of the incision/wound.

The aperture may be of any suitable dimension and may even simply be in the form of guide slits so that an aperture of desired size may be created in the base layer. For use in closing keyhole surgery punctures, an aperture size of between about 5 and about 15 mm in length is desirable. Open surgery incisions are typically larger and so the base layer and aperture may be suitably dimensioned for use in the closure of such incisions. While it is preferred if the aperture fully surrounds the incision or wound, there may be circumstances where this is not desirable or possible. In which case, the aperture size should be selected to be as close to the wound or incision length as possible, with some overlap of the base layer with each end of the incision/wound being tolerated. Alternatively, or in addition, multiple strips may be used to close the wound in a side by side configuration.

It may be desirable to impregnate the base layer or coat the skin-facing surface of the base layer with one or more compositions that promote or aid wound healing, reduce or minimise the likelihood of infection, and/or decrease or minimise the growth of scar tissue. Such compositions may include cytokines, growth hormones, collagen, anti-inflammatories, antiseptics and/or antibiotics.

The upper layer of the device is anchored at one end to the base layer. As with the base layer, the upper layer may be of any suitable shape but, ideally, is of a similar or corresponding shape and dimension to the base layer. In this way, there are fewer edges to catch on clothes etc and become unstuck. The first end of the upper layer should be anchored as permanently as possible to the base layer on one side of the aperture. For example, the end may be (heat) fused, glued or stitched to the base layer, or may be woven from the base layer. This provides a firm anchor which may be used to tension the device.

It will be appreciated that the end will be fixed in a location off-set from the aperture. However, to ensure maximum scope for tensioning of the device (see below) and to reduce puckering of the skin and device around the aperture, the upper end is ideally anchored next to or adjacent the aperture and, therefore, in practice next to or adjacent the wound or incision edge. Alternatively, the end may be anchored close or proximate to the aperture. The greater the distance between the aperture and the anchor point, the greater the likelihood of puckering (and subsequent discomfort for the patient) and lower the tension applied over the aperture.

The second, opposite end of the upper layer is a free end that, in use, is fixed to the base layer so the upper layer covers and substantially closes the aperture. The fixing means on the free end may be of any suitable means, such as adhesive, self-adhesive, Velcro®, barbs or microneedles. As with the base layer, the fixing means should have sufficient strength to hold the upper layer free end onto the base layer for the duration in which the device needs to be applied to the skin.

It is advantageous if the upper layer includes a dressing, such as an absorbent pad in the region where the upper layer overlays the aperture. The dressing absorbs any seepage from the wound and substantially prevents moisture from wicking between the upper and base layers, resulting in release of the upper layer from the base layer as well as applying a protective covering.

The dressing may include one or more compositions to promote or aid wound healing, reduce or prevent bacterial or fungal infection, and/or reduce the likelihood of scar tissue development. For example, the dressing may be an alginate dressing to maintain a moist atmosphere, absorb wound secretions, minimise bacterial contamination and promote healing and the formation of granulation tissue.

In use, the base layer is fixed to the skin so that the aperture surrounds the wound. The base layer is aligned so that the wound is oriented in the aperture perpendicular to the upper layer of the device.

The free end of the upper layer is then pulled in a direction away from the anchored end so the size of the base layer aperture is reduced, bringing the two sides of the wound together and closing the wound. Once the wound has been closed, the free end is fixed to the base layer, without releasing the tension, thereby covering the aperture and wound.

The present invention will now be described in more detail by way of non-limiting example with reference to the figures, in which.

Figure 1:
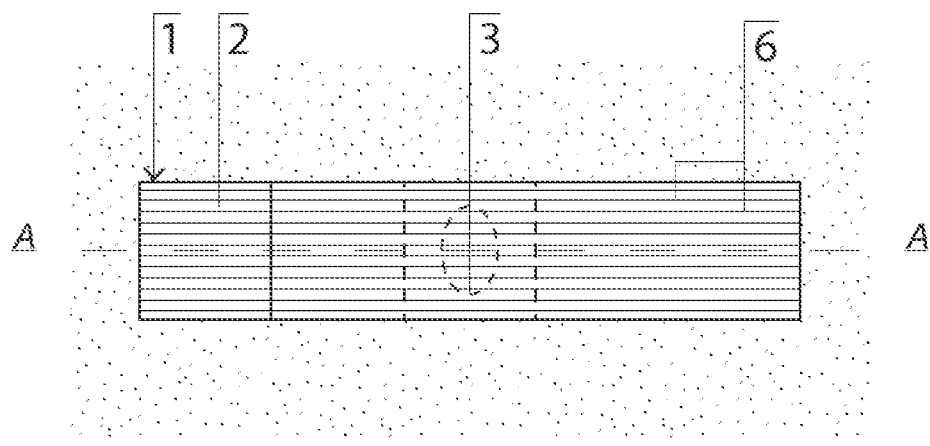
FIG. 1 is a plan view from above of the device of the present invention when closed.
Figure 2:
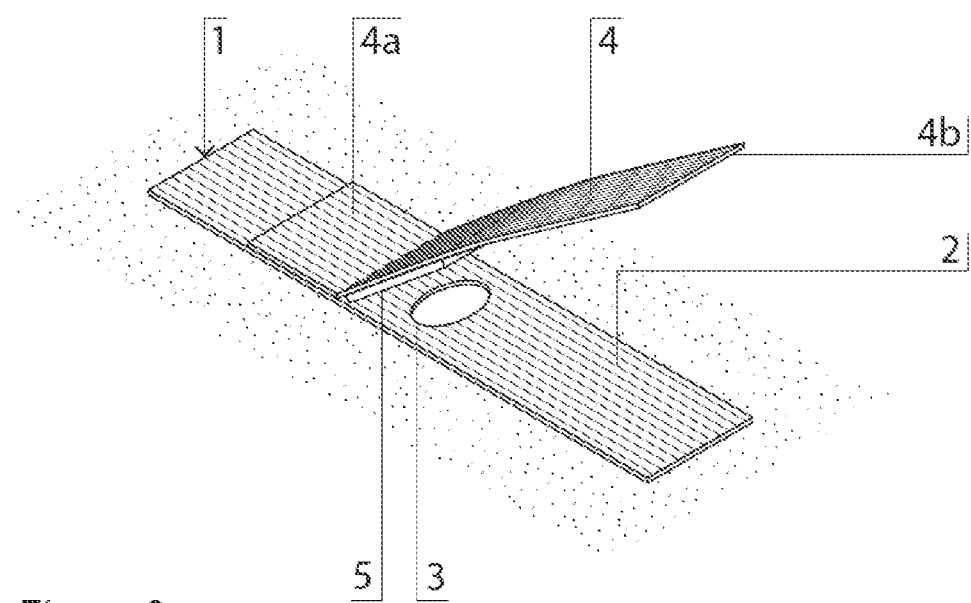
FIG. 2 is a perspective view of the device from above, showing the device in an open configuration.
Figure 3:
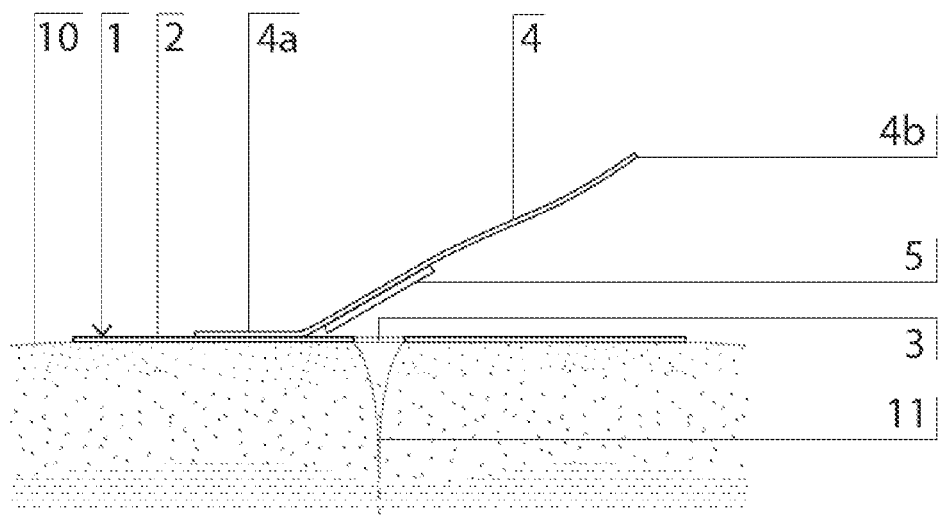
FIG. 3 is a section along line A-A of FIG. 1 showing the device attached to the skin in an open configuration.

The sutureless wound closure device of the present invention is based on a standard adhesive plaster such as a BandAid®. As shown in FIGS. 1 and 2, the device 1 has a base layer 2, an aperture 3 in the base layer 2 and an upper layer 4. In the example illustrated, the device also includes a dressing 5 in the form of an absorbent pad.

The base layer 2 is rectangular in shape having a length that is greater than its width. The layer is made from a porous, non-woven backing which is reinforced with polyester filaments 6. The skin-facing surface is coated with a pressure-sensitive, hypoallergenic adhesive that, in use, adheres the base layer to the skin once a protective backing paper has been removed.

Located in the centre of the base layer 2 is an aperture 3. The aperture 3 is elliptical in shape with the long axis of the ellipse being orientated perpendicular to the length of the base layer 2. In the particular embodiment illustrated, the width of the base layer 2 is dimensioned so that there are two reinforcing filaments 6 on either side of the aperture 3. This ensures that the base layer 2 has sufficient integral strength around the aperture 3. It will be appreciated that the number of reinforcing filaments, if present, will be varied according to the width, desired use, and required strength of the base layer.

The upper layer 4 of the device 1 is similarly dimensioned to the base layer 2 and is made from the same material as the base layer 2. In the embodiment shown in the figures, the upper layer 4 has a length that is approximately three quarters that of the base layer 2. One end 4a of the upper layer 4 is anchored to the upper surface (in use) of the base layer 2 so that an anchor point is located near to the aperture 3 at a distance that is approximately half the width of the aperture 3. End 4a is permanently fixed to the base layer 2 through heat fusion of the two layers. In this way, end 4a cannot be release from the base layer 2.

The opposite end 4b of the upper layer 4 is a free end that has, at its distal portion, a coating of pressure-sensitive self-adhesive on the surface that faces the base layer 2. In between the fixed end 4a and the self-adhesive end 4b is an absorbent pad or dressing 5.

FIGS. 3 to 8 illustrate the device in use. Starting with FIG. 3, the base layer 2 of the device 1 is fixed to the surface of the skin 10 so that the aperture 3 is located around or at the open edges of a wound 11. Upper layer end 4a can be seen anchored to the base layer 2 while the free end 4b is not fixed, allowing the user to see the location of the aperture 3.

Figure 4:
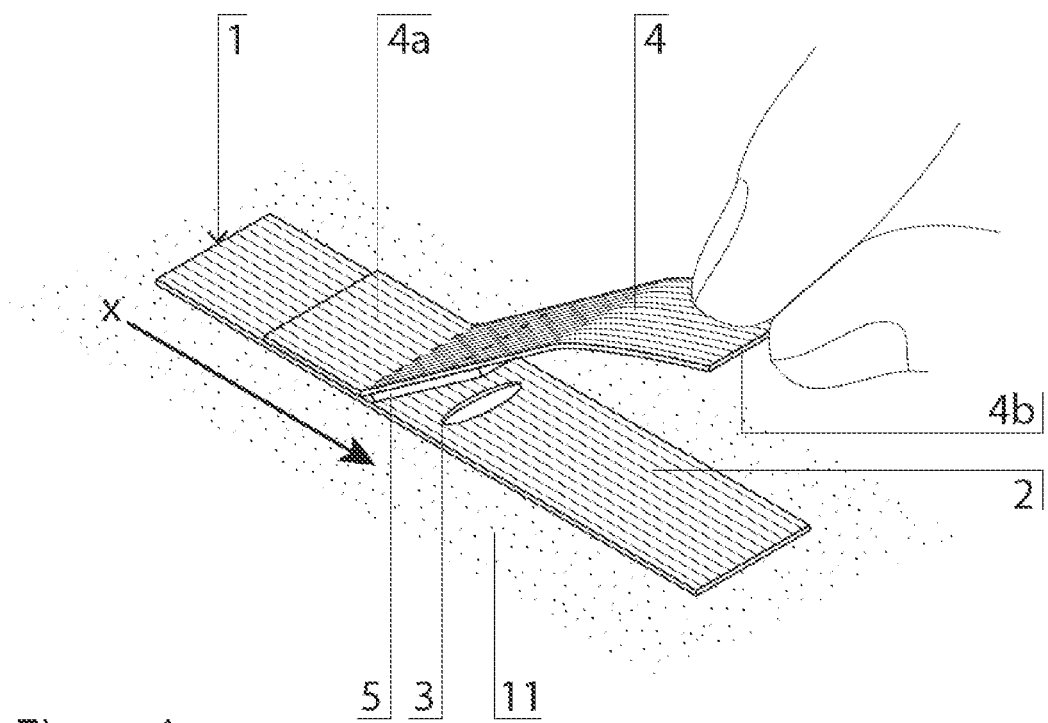
FIG. 4 is a perspective view of the device from above illustrating tensioning of the upper layer.
Figure 5:
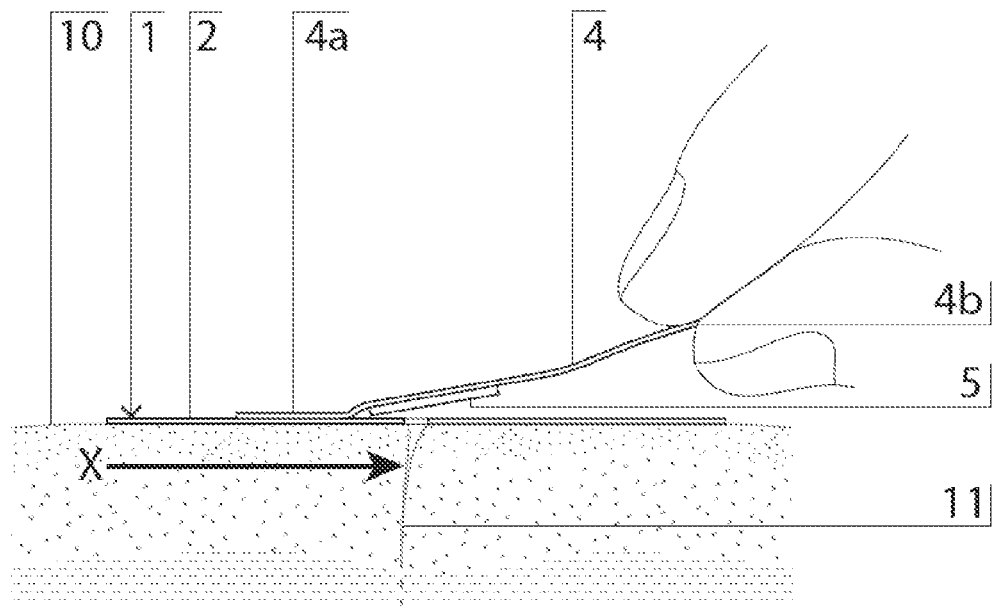
FIG. 5 is a section along line A-A of FIG. 1 showing the device attached to the skin in a partly closed configuration.

Turning to FIG. 4, once the base layer 2 has been suitably located, the free end 4b of the upper layer 4 is grasped by the user and pulled in the direction of Arrow X in the plane of the length of the base layer 2 and perpendicular to the direction of the wound 11. As can be seen in this figure and in FIG. 5, the pulling force narrows the aperture 3 and pulls the sides of the wound 11 towards each other, thereby closing the wound 11.

Figure 6:
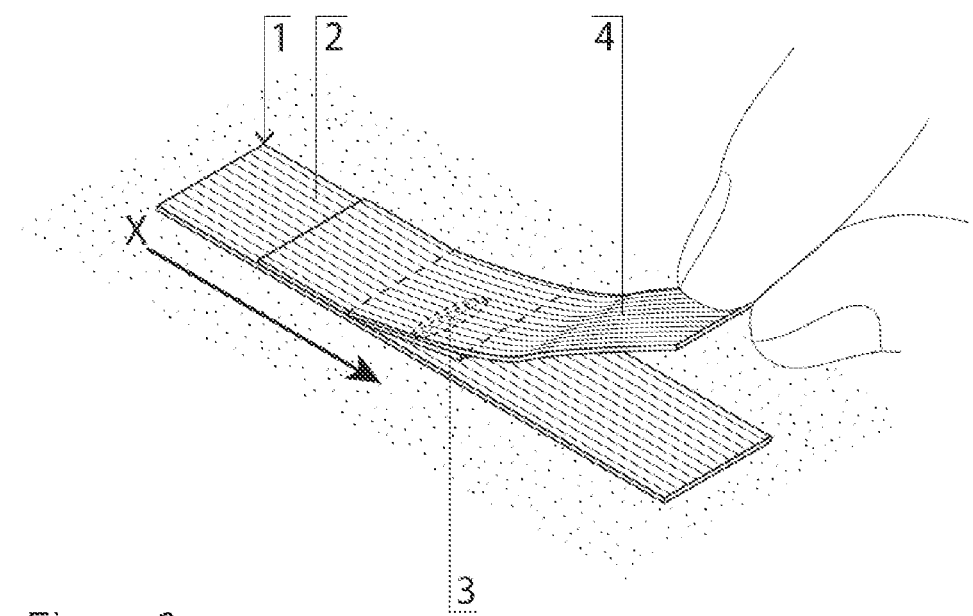
FIG. 6 is a perspective view of the device from above showing the device in a tensioned configuration before the aperture is closed by the upper layer.

As shown in FIG. 6, tension is maintained on the free end 4b of the upper layer 4 as the upper layer 4 is lowered towards the base layer 2.

Figure 7:
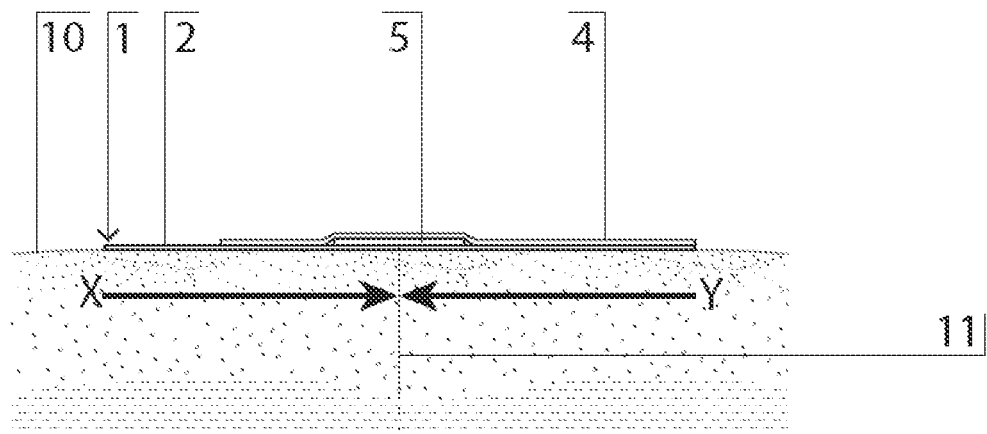
FIG. 7 is a section along line A-A of FIG. 1 showing the device attached to the skin in a closed configuration.
Figure 8:
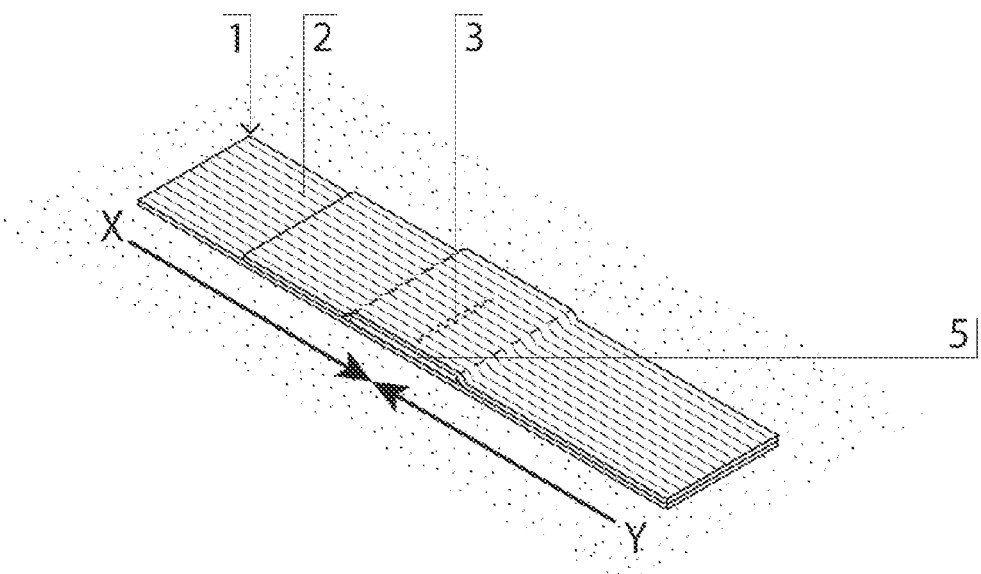
FIG. 8 is a perspective view from above illustrating the device when closed in situ.

FIGS. 7 and 8 show the device in a closed configuration in which the sides of the wound 11 are held together and dressing 5 covers the aperture 3. The dressing 5 is located to capture any seepage from the wound 11 so that capillary forces between the base and upper layers 2, 4 do not come into effect, fluid is not wicked between the layers, and so the seal between the upper and lower layers 2, 4 is maintained.

As shown in FIG. 8, adhesion of the upper layer 4 to the base layer 2 maintains a tension (illustrated by Arrows X and Y) on both sides of the wound 11, keeping the wound 11 closed and allowing the cut skin to knit together and heal with minimal scar formation.

Figure 9:
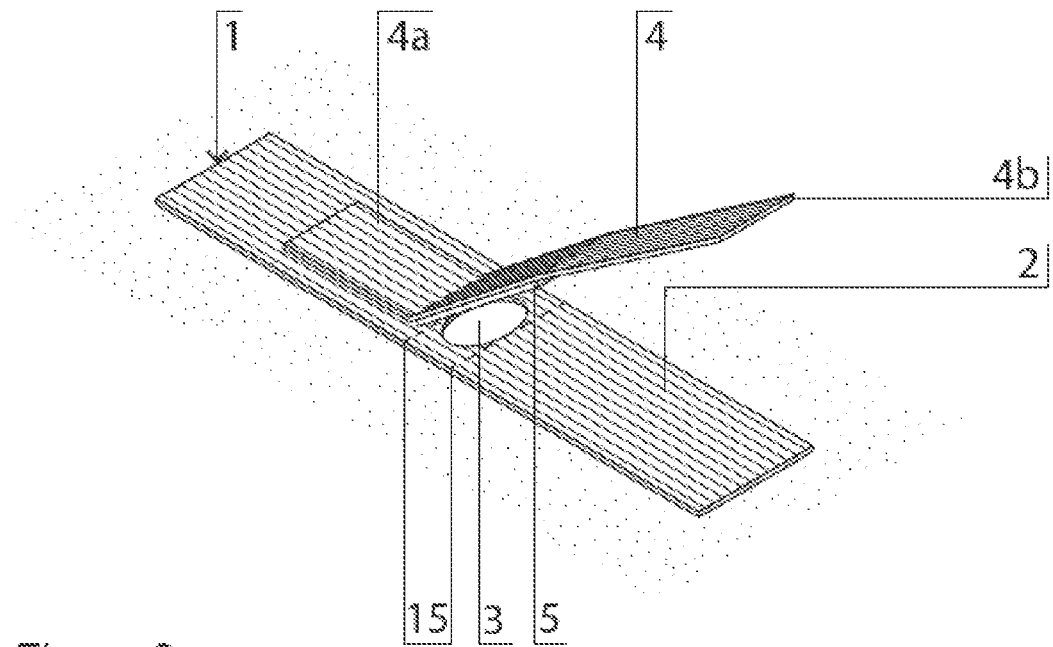
FIG. 9 is a perspective view of an alternative embodiment of the device from above, showing the device in an open configuration.
Figure 10:
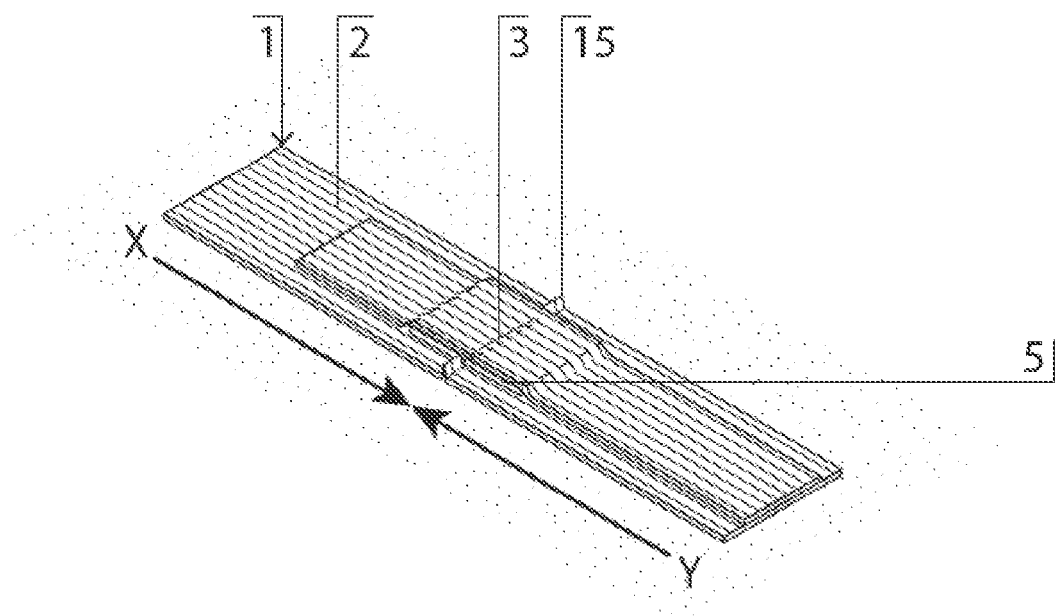
FIG. 10 is a perspective view from above illustrating the alternative embodiment of the device when closed in situ.

In an alternative embodiment, the base layer 2 further includes a flexible portion 15 on either side of the aperture 3. In the embodiment shown in FIG. 9, the flexible portion 15 is made from a thinner material than the base layer 2 and has no or minimal adhesive. This allows the flexible portion 15 to concertina or fold upwards away from the skin when the aperture 3 is closed by the top layer 4. The top layer 4 is dimensioned such that flexible portion 15 is able to fold upwards on either side of the top layer 4, as illustrated in FIG. 10. In particular, the top layer 4 is dimensioned to have a width that substantially matches the width or diameter of the aperture 3. In this way, the device 1 does not fold the underlying skin, thereby enhancing the effectiveness of the device 1 on the skin and adding comfort to the patient. An alternative to the flexible portion 15 could be a waisted portion.

The present invention finds particular application in the field of keyhole surgery but it will be appreciated that the closure device may be equally suitably used for larger wounds, such as medium-sized open surgery wounds of a size say about 10-15 mm. Equally, a large or larger wound may be closed using a number of closure devices of the present invention.

The invention claimed is:

1. A sutureless wound closure device comprising:
   a) a base layer for attaching the device to skin; and
   b) an upper tensioning layer having a first end anchored to the base layer and a second, opposite free end configured to attach to the base layer,
   wherein the base layer defines an aperture entirely surrounded by a material of the base layer, and, when in use, the aperture is entirely covered by the upper tensioning layer, the aperture having a width and a length greater than the width, and the aperture being sized to surround an incision or wound in the skin; and
   wherein attaching the second end of the upper tensioning layer to the base layer narrows the width of the aperture.

2. The device according to claim 1, wherein the base layer is substantially rectangular in shape having a length greater than its width.

3. The device according to claim 1, wherein the base layer includes adhesive, self-adhesive, barbs or microneedles on its skin-facing surface to attach the device to the skin.

4. The device according to claim 1, wherein the aperture in the base layer is centrally located in a width and a length of the base layer.

5. The device according to claim 1, wherein the aperture has an elliptical shape, orientated perpendicular to a length of the base layer.

6. The device according to claim 1, wherein the aperture is between 3 mm and 15 mm in length.

7. The device according to claim 1, wherein the base layer includes one or more compositions to promote or aid wound healing, reduce or minimise the likelihood of infection, and/or decrease or minimise the growth of scar tissue.

8. The device according to claim 1, wherein the first end of the upper tensioning layer is anchored to the base layer on one side of the aperture.

9. The device according to claim 8, wherein the first end of the upper tensioning layer is anchored next to the aperture.

10. The device according to claim 8, wherein the first end of the upper tensioning layer is anchored proximate to the aperture.

11. The device according to claim 1, wherein the second end of the upper tensioning layer includes an adhesive, a self-adhesive, Velcro®, barbs, or microneedles.

12. The device according to claim 1, wherein the upper tensioning layer further includes a dressing located to cover the aperture when in use.

13. The device according to claim 12, wherein the dressing includes at least one composition to promote or aid wound healing, reduce or minimise the likelihood of infection, and/or decrease or minimise the growth of scar tissue.

14. The device according to claim 1, wherein the base layer includes a flexible portion on either side of the aperture.

15. The device according to claim 14, wherein the flexible portion does not attach to the skin.

16. The device according to claim 1, wherein the aperture is the only aperture in the base layer.

17. The device according to claim 1, wherein the device is configured such that all portions of a bottom, skin-facing surface of the base layer are capable of touching the skin.

18. The device according to claim 17, wherein all of the bottom of the base layer is configured to lie flush against the skin.

* * * * *